(12) United States Patent
Senter et al.

(10) Patent No.: US 12,016,401 B2
(45) Date of Patent: Jun. 25, 2024

(54) AEROSOL PRESSURIZED INHALATION DELIVERY DEVICE AND METHODS FOR MANUFACTURE AND USE OF THE SAME

(71) Applicant: Air 2 LLC, Centennial, CO (US)

(72) Inventors: Robert L. Senter, Centennial, CO (US); Robert E. Matuszewski, Centennial, CO (US)

(73) Assignee: Air 2, LLC, Centennial, CO (US)

( * ) Notice: Subject to any disclaimer, the term of this patent is extended or adjusted under 35 U.S.C. 154(b) by 0 days.

(21) Appl. No.: 18/300,992

(22) Filed: Apr. 14, 2023

(65) Prior Publication Data

US 2023/0329354 A1    Oct. 19, 2023

Related U.S. Application Data

(60) Provisional application No. 63/331,497, filed on Apr. 15, 2022.

(51) Int. Cl.
| | | |
|---|---|---|
| A24F 42/20 | (2020.01) | |
| A24B 15/167 | (2020.01) | |
| A24F 42/60 | (2020.01) | |
| A61M 15/00 | (2006.01) | |
| A61M 15/06 | (2006.01) | |

(52) U.S. Cl.
CPC .......... A24F 42/20 (2020.01); A24B 15/167 (2016.11); A24F 42/60 (2020.01); A61M 15/0035 (2014.02); A61M 15/009 (2013.01); A61M 15/06 (2013.01); A61M 2205/586 (2013.01)

(58) Field of Classification Search
None
See application file for complete search history.

(56) References Cited

U.S. PATENT DOCUMENTS

| | | | | |
|---|---|---|---|---|
| 2006/0211589 A1* | 9/2006 | Godfrey et al. | ....... | B65D 83/48 510/161 |
| 2007/0051363 A1* | 3/2007 | Andrus et al. | ..... | A61M 15/0088 131/270 |
| 2008/0138423 A1* | 6/2008 | Gonda | ................. | A61M 16/10 514/343 |
| 2016/0121059 A1* | 5/2016 | Child et al. | ......... | A61M 15/002 128/200.23 |
| 2017/0252300 A1* | 9/2017 | Modi | ................... | A61K 31/352 |
| 2020/0156826 A1* | 5/2020 | Kilduff et al. | ....... | B65D 43/162 |
| 2023/0080276 A1 | 3/2023 | Zambelli | | |

FOREIGN PATENT DOCUMENTS

| | | | | |
|---|---|---|---|---|
| GB | 2544477 | * | 5/2017 | ........ A61M 15/0021 |
| GB | 2544477 A | * | 5/2017 | ........ A61M 15/0021 |

OTHER PUBLICATIONS

E. Callard Preddy et al,"History of Inhaler Devices" excerpt from Inhaler Devices, taken from the ScienceDirect Website entitled "Metered Dose Inhaler";https://www.sciencedirect.com/topics/pharmacology-toxicology-and-pharmaceutical-science/metered-dose-inhaler. Printed from the Internet on Feb. 10, 2024 (Year: 2013).*

* cited by examiner

Primary Examiner — Dionne W. Mayes
(74) Attorney, Agent, or Firm — FisherBroyles LLP; Ian R. Walsworth (57) ABSTRACT

The present invention improves and enhances the delivery of one of an aerosolized or micellized formula by use of an aerosol pressurized inhalation delivery device. The device may include one or more replaceable or reusable components, including but not limited to a canister and a battery. Methods for using the device to deliver a controlled dosage via the delivery device are also described herein.

8 Claims, 12 Drawing Sheets

AEROSOL PRESSURIZED INHALATION DELIVERY DEVICE AND METHODS FOR MANUFACTURE AND USE OF THE SAME

CROSS REFERENCE TO RELATED APPLICATIONS

The present application claims priority under 35 U.S.C. § 119(c) to U.S. Provisional Patent Application Ser. No. 63/331,497, filed Apr. 15, 2022, the entirety of which is incorporated herein.

FIELD OF THE INVENTION

Aspects of the present disclosure relate generally to the field of medical devices, and more particularly to a device for delivering and related systems and methods, and more particularly a pressurized inhalation delivery device that eliminates a cartridge or reservoir or pod, the heating element and power source or battery.

BACKGROUND

The Center for Disease Control and Prevention ("CDC") validates that smoking can cause cancer, most often lung cancer, and then block the human body from fighting the disease. It is well known in the art that the poisons in cigarette smoke can affectively weaken the body's immune system, creating a greater challenge to kill cancer cells which grow and multiple over time. More specifically, the poisons in tobacco smoke can damage or change a cell's DNA and once damaged, those cells can begin growing out of control and create a cancer tumor. In addition, vaping has become increasingly popular in recent years among teenagers and young adult populations, and the known additive nature of nicotine among youth and young adults has developed into a major health concern. These and related issues have become a considerable health risk, including for people who do not smoke or vape but are exposed to the second-hand smoke of another.

Vaping is a process of aerosolizing a solution and inhaling it into the lungs using an electronic cigarette (e-cigarettes) or other vaping device that serves as an alternative to conventional smoking. During the vaping process, e-cigarettes heat a liquid into an aerosol that the user inhales into their lungs, and commonly comprise a replaceable cartridge. A typical c-cigarette cartridge (also referred to as a reservoir or pod) contains four basic ingredients: water; nicotine; flavorings; and, a propylene or vegetable glycerin base commonly referred to as e-liquid. Consumers may choose from a wide variety of vapes and e-cigarette products that contain nicotine, flavorings, and other additives.

There are a variety of devices known in the art for vaping. For example, e-cigarettes or "e-cigs," "cigalikes," "e-hookahs," "mods," "vape pens," "vapes," and "tank systems" are vaping devices existing in the art today. By way of example, U.S. Pat. No. 8,511,318 describes an e-cigarette device that is comprised of a cylindrical shell containing an e-cigarette cell, a nicotine solution, a control circuit, and an electro-thermal vaporization nozzle. The device allows a person to suck air through an air suction fitting on one end of the shell, which the patent describes as beneficial as it eliminates tar from the nicotine solution and reduces the risk of fire between inhalations. Another example is provided in U.S. Pat. No. 9,737,093, which describes an e-cigarette device having a separate cartridge and vaporizer unit. The separate cartridge unit comprises a liquid with a seal that keeps the liquid safely within the cartridge tube, but may be pierced by a piercer prior to use. The piercer is described as part of the vaporizer unit, which further comprises a heater and an electronic circuit electrically connected to a battery. Notably, the prior art does not disclose a device for providing an aerosolized and/or micellized liquid nicotine formula. The prior art also fails to disclose an actuator that provides precise dosage such that a known amount of the liquid may be inhaled with each depression/activation. There are other problems with the prior art, including malfunctions with the electronic circuitry, battery failure, mechanical failure, leaking and/or harmful exposure to the liquid or other substance contained by the cartridge, and other problems addressed by the present disclosure.

Although numerous other prior art solutions have attempted to improve upon vaping and e-cigarette devices, none of the solutions effectively provides an aerosolized delivery device that is accurate, reproducible, that provides a known amount of liquid, including a dosage of micellized liquid nicotine formula, which may be inhaled with each depression/activation, that otherwise eliminates the varying dosing volumes created in prior art vaping and e-cigarettes. A number of other challenges and deficiencies in the art still persist or remained completely unsolved. It is with respect to these and other problems that the present disclosure is contemplated, as will be described in greater detail below.

SUMMARY

Aspects of the present disclosure relate to an aerosol pressurized inhalation delivery device having an actuator, metered valve, receptacle housing and aluminum canister allowing a micellized liquid nicotine formula to be expelled through the actuator discharge nozzle by depressing the actuator discharge finger slide control and inhaling the formula into the lungs through the mouthpiece. Depressing the actuator discharge finger slide control delivers a known amount of total formula passing from the metered valve through the actuator discharge nozzle ensuring an accurate and known amount of micellized liquid nicotine formula is inhaled with each depression/activation eliminating the varying dosing volumes created in vapes and e-cigarettes. The aerosol pressurized inhalation delivery device eliminates the use of cartridges or reservoirs or pods, the heating element and power source or battery and addresses the deficiencies of inaccurate and inconsistent dosing with vaping by utilizing a microliter metered valve that dispenses a known volume of micellized liquid nicotine formula containing fractionally less nicotine while delivering an equivalent feeling of pleasure to the user.

According to another aspect of the present disclosure, the invention relates to an aerosol pressurized inhalation delivery device having an actuator with a discharge finger slide control and mouthpiece, metered valve, receptacle housing, and aluminum canister containing a micellized liquid nicotine formula and a propellant such as pharma grade 1,3,3,3,-Tetrafluropropene, HFO 1234ze allowing the micellized liquid nicotine formula to be expelled as a nano mist and inhaled into the lungs with the depression of the actuator discharge finger slide control.

According to another aspect of the present disclosure, the device comprises an aluminum canister pressurized with a propellant, such as pharma grade 1,3,3,3,-Tetrafluropropene, HFO 1234ze, and may further comprise a crimped metered valve attached to the canister. In use, the canister may be inserted into a receptacle housing, which in turn allows an actuator to discharge a known dosage. The device and 
actuator may further comprise a childproof safety guard to be placed over the actuator. The receptacle housing may further comprise one or more finger slide control channels for providing a further safety feature with the device.

According to one specific aspect, the present disclosure relates to a An aerosol pressurized inhalation delivery device comprising: a metered valve crimped to an aluminum canister; an actuator having actuator discharge finger slide controls; an actuator positioned over a metered valve; a micellized liquid nicotine formula residing within the aluminum canister; a liquid propellant residing within the aluminum canister; an aluminum canister residing within a receptacle housing; and an actuator locked into a receptacle housing.

According to yet another specific aspect, the present disclosure relates to a method of delivering a nano mist micellized liquid formula comprising: coupling a metered valve on a canister containing micellized liquid formula; placing the canister and metered valve into a receptacle housing; positioning an actuator above the metered valve; activation the actuator by pressing actuator against the metered valve; piercing a diaphragm on the canister with a valve stem associated with the metered valve; delivering, under pressure, a volume of micellized liquid formula from the canister, through the metered valve, into an expansion chamber; delivering the volume of micellized liquid formula from the expansion chamber through a discharge nozzle.

According to one aspect, the invention comprises a non-combustible, smoke-free device for delivering a nano mist aerosolized nicotine (which according to one embodiment is 99.9% pure tobacco). In embodiments, the device has no heat, no battery, no oil and greatly reduced the risk of harm during use of the device. The device preferably comprises a proprietary water-soluble micellized liquid nicotine formula that reduces the nicotine content by up to 80% compared to electronic nicotine delivery systems ("ENDS").

According to embodiments, the device may be manufactured utilizing a process or processes consistent with, or otherwise in observation of, Environmental Protection Agency and U.S. Food & Drug Administration regulatory guidelines. In embodiments, all ingredients of the micellized liquid nicotine formula are FDA and GRAS compliant, by the Natural & Non-Prescription Product Group. In embodiments, the invention is manufactured utilizing pharmaceutical grade equipment and components.

The devices and components described herein may comprise one or more of a polymeric material and a metallic material. More particularly, the present disclosure may be constructed of materials known to provide, or predictably manufactured to provide the various aspects of the present disclosure. These materials may include, for example, carbon fiber, ABS plastic, polyurethane, polyethylene, photopolymers, resins, fiber-encased resinous materials, rubber, latex, synthetic rubber, synthetic materials, polymers, and natural materials. These materials may further include, for example, stainless steel, titanium alloy, aluminum alloy, chromium alloy, and other metals or metal alloys.

In one embodiment, at least a portion the delivery device described herein is reusable. Optionally, a portion of the delivery device is disposable, but in other embodiments the entire delivery device may be reusable or disposable after a set number of uses.

One having skill in the art will appreciate that embodiments of the present disclosure may have various sizes. The sizes of the various devices or their components may be sized based on various factors including, for example, the anatomy of the user, such as the height and weight of the person operating the device, or other physical features of replaceable or reusable components used with the devices described herein, including, for example, width, length and thickness, and the intended dosage(s) provided by the device.

These and other features, utilities, and advantages of the various embodiments of the present invention will be apparent from the following more particular descriptions of the embodiments of the invention as illustrated in the accompanying drawings and defined in the appended claims.

Certain terms are used throughout the following description and claims to refer to a particular system or device components. As one skilled in the art will appreciate, companies may refer to a component by different names. This document does not intend to distinguish between components that differ in name but not function.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being approximations which may be modified in all instances as required for a particular application of the novel apparatus described herein.

In the following disclosure, the use of "including," "comprising," or "having" and variations thereof herein is meant to encompass the items listed thereafter and equivalents thereof as well as additional items. Accordingly, the terms "including," "comprising," or "having" and variations thereof can be used interchangeably herein. In the claims, the terms "including" and "comprising" are used in an open-ended fashion, and thus should be interpreted to mean "including, but not limited to. . . . "

The term "a" or "an" entity, as used herein, refers to one or more of that entity. As such, the terms "a" (or "an"), "one or more" and "at least one" can be used interchangeably herein.

The terms "determine," "calculate," and "compute," and variations thereof, as used herein, are used interchangeably and include any type of methodology, process, mathematical operation, or technique.

The term "couple" or "couples" is intended to mean either an indirect or direct connection. When used in a mechanical context, if a first component couples or is coupled to a second component, the connection between the components may be through a direct engagement of the two components, or through an indirect connection that is accomplished via other intermediate components, devices and/or connections. In addition, when used in an electrical context, if a first device couples to a second device, that connection may be through a direct electrical connection, or through an indirect electrical connection via other devices and connections. Connections can occur in a unidirectional, bidirectional or variable directional manner over all known means of network connectivity.

By way of providing additional background, context, and to further satisfy the written description requirements of 35 U.S.C. § 112, the following are incorporated by reference in their entireties for the express purpose of explaining and further describing the various devices and apparatus that may be associated with aerosol and micellized nicotine delivery, in general: U.S. Pat. Nos. 8,511,318; 9,737,093; and, 11,172,704.

The Summary is neither intended nor should it be construed as being representative of the full extent and scope of the present disclosure. The present disclosure is set forth in various levels of detail in the Summary as well as in the attached drawings and the Detailed Description and no limitation as to the scope of the present disclosure is intended by either the inclusion or non-inclusion of elements, components, etc. in this Summary. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below.

BRIEF DESCRIPTION OF THE DRAWINGS

Many aspects of the disclosure can be better understood with reference to the following drawings. While several implementations are described in connection with these drawings, the disclosure is not limited to the implementations disclosed herein. On the contrary, the intent is to cover all alternatives, modifications, and equivalents.

In certain instances, details that are not necessary for an understanding of the disclosure or that render other details difficult to perceive may have been omitted. It should be understood, of course, that the disclosure is not necessarily limited to the particular embodiments illustrated in the following Figures. In the drawings.

It should be understood that the drawings are not meant to be and/or are not necessarily to scale.

For ease of reference, the following is a listing of components depicted in the drawing figures, some of which are described in greater detail herein:

100 aerosol inhaler delivery device
102 Actuator
104 actuator mouthpiece
106 actuator discharge area
108 actuator discharge nozzle
110 actuator discharge channel
112 actuator valve sleeve
114 actuator discharge finger slide control
116 actuator discharge finger slide control grip ridges
118 actuator receptacle locking clip actuator discharge finger slide control child
120 proof safety guard
122 child proof safety guard channel locks
124 child proof safety guard plastic compression clip
126 child proof safety guard grips
128 metered valve
130 metered valve stem
132 metered valve internal gasket
134 metered valve external gasket
136 metered valve mounting cup
138 metered valve spring
140 metered valve metering chamber
142 metered valve dip tube
144 receptacle housing
146 receptacle housing actuator rim
148 receptacle housing finger slide control channels
150 receptacle actuator locking edge
152 receptacle canister security ridges
154 receptacle cylindrical grips
156 aluminum canister
158 aluminum canister lip
160 aluminum canister throat
162 aluminum canister rim
164 liquid propellant
166 micellized liquid nicotine formula
168 air pocket

DETAILED DESCRIPTION

The following disclosure is directed to various embodiments, including those depicted in FIGS. 1-17 appended hereto. Embodiments described herein relate to an aerosol pressurized inhalation delivery device (and methods for fabricating and using the same) that delivers a precise dose of micellized liquid nicotine formula with the depression of the actuator discharge finger slide control of the actuator. The actuator is secured to the metered valve which is crimped to an aluminum canister. The aluminum canister is positioned inside the receptacle housing and can be Fluorinated Ethylene Propylene (FEP) coated to avoid any chemical interaction between the micellized liquid nicotine formula and aluminum canister.

The aerosol pressurized inhalation delivery device eliminates the use of a power source or battery which as used in prior art devices has been known to explode without warning and cause serious injuries including burns, broken bones or even death. The alternative use of a propellant, such as pharma grade 1,3,3,3,-Tetrafluropropene, HFO 1234ze, which is chlorofluorocarbon free and approved by the FDA for use in metered-dose inhalers for the treatment of asthma and other pulmonary obstructive diseases, eliminates the aforementioned safety concerns.

Placing the aluminum canister into the receptacle housing protects the aluminum canister from impact and allows the actuator to be positioned over the receptacle housing and locked into a secure position via the actuator receptacle locking clip and receptacle actuator locking edge.

An actuator discharge finger slide control child proof safety guard can be snapped into position over the receptacle housing finger slide control channels eliminating the ability to depress the actuator discharge finger slide control downward providing a child proof aerosol pressurized inhaler deliver device.

The metered valve is preferably crimped onto the aluminum canister with, for example, a metal crimping collette, which couples the metered valve mounting cup of the metered valve against the rim of the aluminum canister. The crimp or an equivalent connector securely holds the metered valve onto the aluminum canister which once gassed can maintain, by way of example but not limitation, approximately 75 psi (pounds per square inch) pressure inside the aluminum canister.

The actuator is preferably made from high quality plastic or resinous material and contains a discharge finger slide control that once depressed activates the metered valve and delivers an exact volume of micellized liquid nicotine formula to the user through the mouthpiece. The actuator, once fully depressed downward on the metered valve, allows the metered valve's valve stem to be pushed downward into the canister. The micellized liquid nicotine formula is thereby forced, under approximately 72 psi, through the metering chamber and into the expansion chamber. Once the volume of micellized liquid nicotine formula is passed into the expansion chamber, the volume is delivered through the nano mist discharge nozzle.

The volume of liquid micellized formulation delivered with each activation of the actuator is preferably within the range of 50 to 100 microliters. In one embodiment, the volume is precisely controlled at 100 microliters by utilizing a metered valve configured to release 100 microliters. In another embodiment, the volume is precisely controlled at 65 microliters. According to one particular aspect, the method of delivering a known volume of micellized liquid nicotine formula is as follows: once the valve stem has been fully depressed, a valve stem side piercing passes through a diaphragm. The volume of micellized liquid nicotine formula enters into the metering chamber, which includes a precise, controlled volume of micellized liquid nicotine formula and propellant based on the configuration of metered valve.

From the first actuation until the last actuation, the pressure in the canister remains constant allowing a controlled, consistent and precise dose of liquid micellized formula and propellant to be expelled through the actuators discharge nozzle.

In one aspect, the combination of the micellized liquid nicotine formula and propellant, which in one embodiment may be a propellant known commercially as HFA 134a, becomes miscible, visibly clear, having a viscosity similar to water, homogenous mixture, which makes it easier to deliver a precise metered dose of the combined micellized liquid nicotine formula and propellant through the actuator discharge nozzle.

In embodiments, the nicotine formula is preferably micellized, a phase separation of water from oil. This process, referred to herein as micellization, converts an otherwise oil-based product and their ingredients and making them bio-absorbable or "bio available" to the body, without changing their molecular form and structure.

Through research and experimentation, the applicant has found that micelles formulated, full spectrum hemp oil ("FSHO") has demonstrated significantly more bioavailability than non-micelles, unformulated hemp-based oils. This means that the FSHO, using micelle technology is more effective, delivering better than 85% absorption to the body, GI tract and/or skin, with a quicker onset than that of traditional, lower dose, FSHO based, or Cannabidiol based products. The same will apply to Tetrahydrocannabinol oil based micellized formulas.

The spirit of this disclosure, in one particular aspect, is to eliminate the use of cartridges or reservoirs or pods, heating elements and power sources or batteries in prior art devices, such as vape units, and to replace the corresponding formulas containing nicotine, flavorings, and propylene glycol with a safer known dispensed micellized liquid nicotine formula that dramatically decreases the nicotine percentage oral uptake, delivers better absorption to the body, and helps minimize the known threats of cancer to the user.

E-cigarette's use of a battery, the most common called "18650" batteries, heat up the nicotine formula, flavorings and other chemicals and turn them into a vapor the user can breathe. This vapor can contain formaldehyde, heavy metals and other particles that can cause cancer and loge themselves in the users' deepest parts of the lungs. The present disclosure eliminates the battery or power supply required by e-cigarettes and vaping devices.

In the "News in Health" article presented by the NIH, National Institute of Health, https://newsinhealth.nih.gov/2020/05/risks-vaping, the risk of vaping is described and acknowledgment is made that "Studies suggest nicotine vaping may be less harmful than traditional cigarettes when people who regularly smoke switch to them as a complete replacement. But nicotine vaping could still damage your health, according to the NIH, because a person must necessarily inhale propylene glycol, vegetable glycerin, and flavorants that were meant to be eaten but not inhaled, not to mention nicotine. When vaping, all of those chemicals are heated up by the power supply and reactor, which may cause those components to turn into other potentially dangerous chemicals.

An object of this disclosure, in another aspect, is to create a safer aerosol pressurized inhalation delivery device compared to smoking or vaping using similar components to those employed in pressurized metered dose inhalers, pMDI's, and having a micellized liquid nicotine formula that once inhaled into the lungs delivers greater absorption to the body and significantly lowers the percentage of nicotine inhaled while providing a similar feeling of pleasure for the user.

Figure 1:
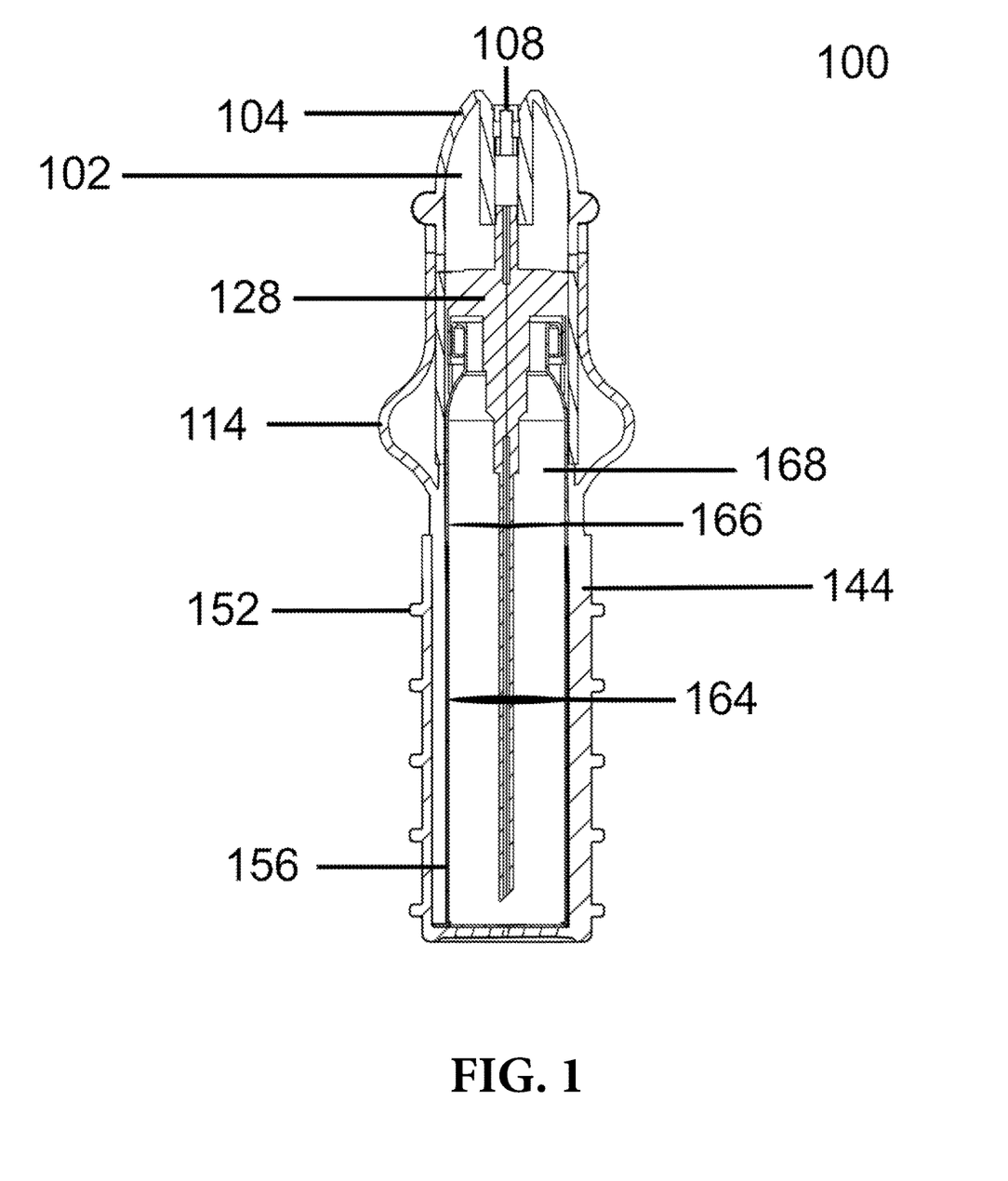
FIG. 1 is a cross-sectional view of a first embodiment of the delivery device according to a preferred embodiment depicting an actuator, metered valve, receptacle housing and canister.

Various aspects of the present disclosure are shown in FIGS. 1-21. FIG. 1 is a cross-sectional view of aerosol pressurized inhaler delivery device 100 comprising aluminum canister 156 positioned securely inside receptacle housing 144 having metered valve 128 crimped to aluminum canister 156 allowing pressurized gas such as, pharma grade 1,3,3,3,-Tetrafluropropene, HFO 1234ze, 164 and micellized liquid nicotine formula 166 to be introduced into aluminum canister 156. Depressing discharge finger slide control 114 allows propellant 164 and micellized liquid nicotine formula 166 to pass through metered valve 128 and actuator discharge nozzle 108 creating a nano mist spray inhaled through mouthpiece 104.

Figure 2:
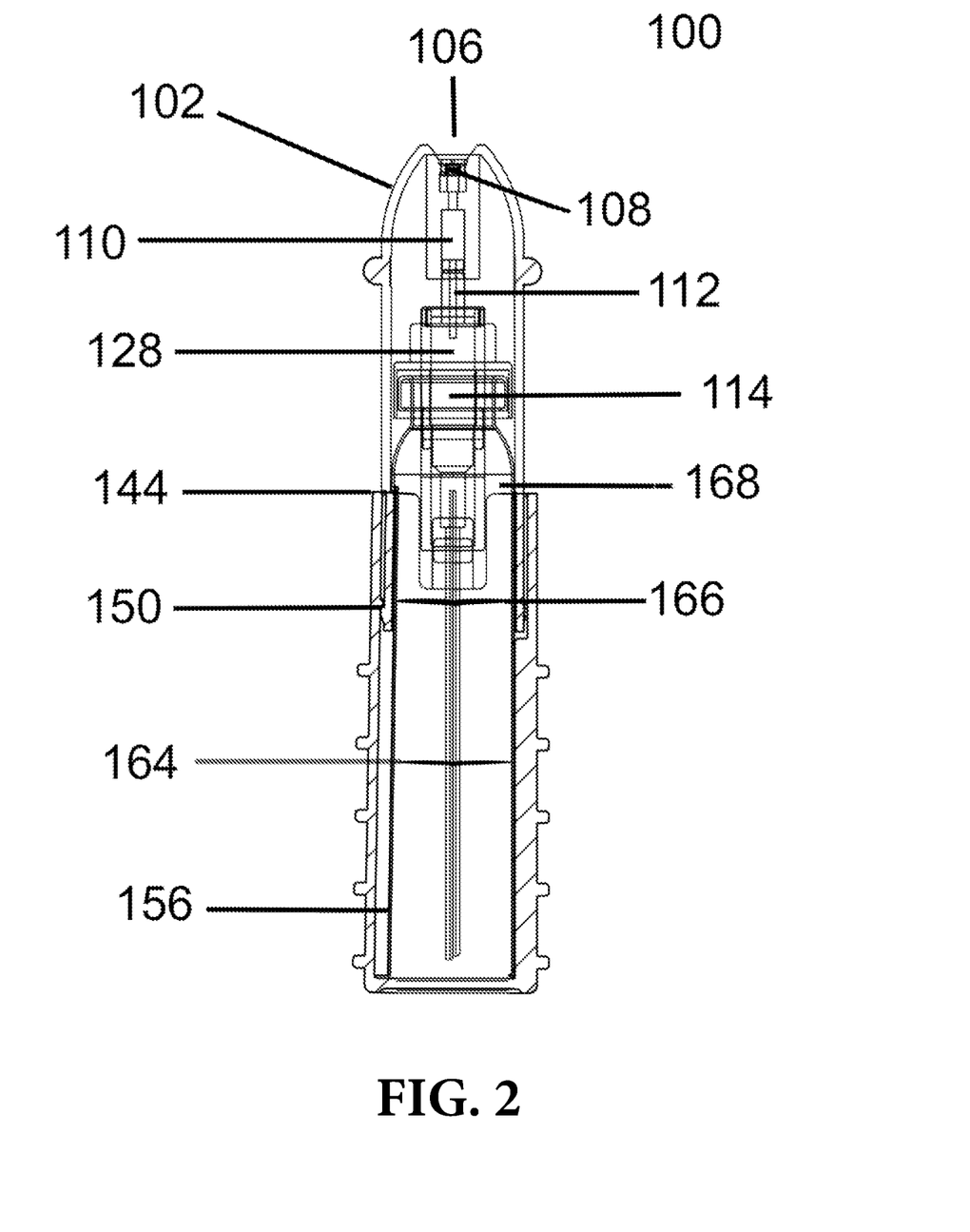
FIG. 2 is a side view of the delivery device shown in FIG. 1.

FIG. 2 is a cross sectional side view of aerosol pressurized inhaler delivery device 100, actuator 102, metered valve 128, receptacle housing 144, aluminum canister 156, actuator discharge finger slide control 114, air pocket 168, micellized liquid nicotine formula 166 and liquid propellant 164. The volume of liquid propellant 164 is pre-determined considering the volume of the micellized liquid nicotine formula 166 introduced into the aluminum canister 156. It is known by those skilled in the art that a pressurized liquid substance such as pharma grade 1,3,3,3,-Tetrafluropropene, HFO 1234ze or other liquid propellant introduced into aluminum canister 156 also containing micellized liquid nicotine formula 166 will expand as the outside temperature increases. The pre-determined volume of liquid propellant 164 and pre-determined volume of micellized liquid nicotine formula 166 introduced into the aluminum canister 156 via a gassing machine is adjusted to allow expansion of the contents when increased outside temperatures are exerted on aluminum canister 156. The starting pressure of prefilled aluminum canister 156 is approximately 75 psi, (pounds per square inch), at an outside temperature of approximately 72 degrees Fahrenheit or 22.2 Celsius. Micellized liquid nicotine formula 166, less dense than liquid propellant 164, rises above liquid propellant 164 inside aluminum canister 156. Air pocket 168 allows safe expansion of liquid propellant 164 and micellized liquid nicotine formula 166 inside aluminum canister 156 once outside temperatures increases beyond 72 degrees Fahrenheit or 22.2 Celsius.

Figure 3:
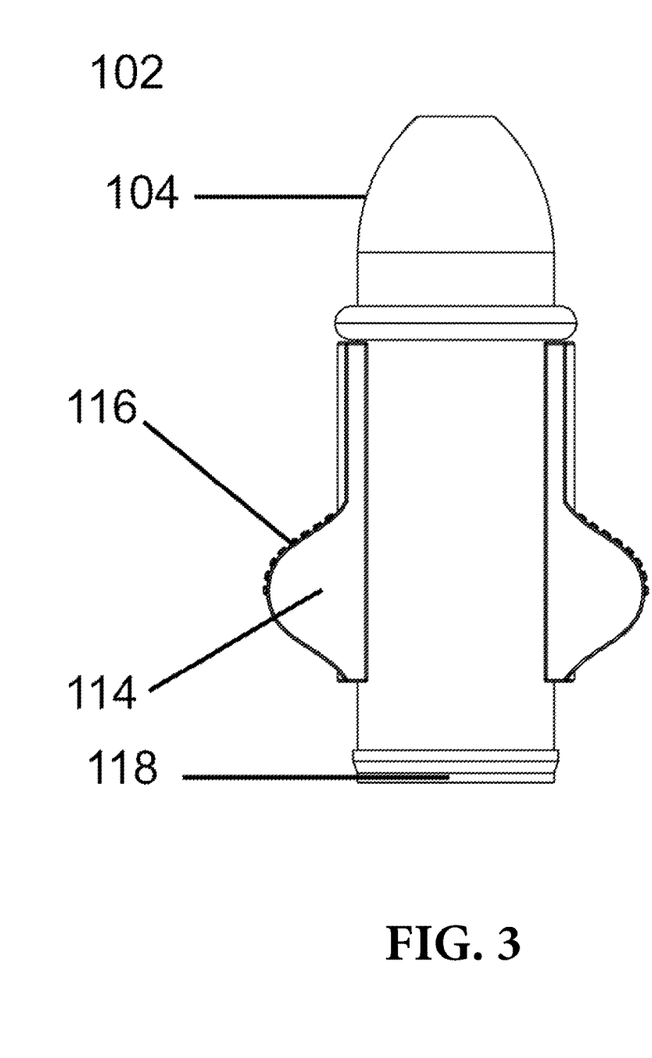
FIG. 3 is a side view of the actuator.

FIG. 3 is a side view of actuator 102, showing mouthpiece 104, actuator discharge finger slide control 114 having grip ridges 116 and actuator receptacle locking clip 118.

Figure 4:
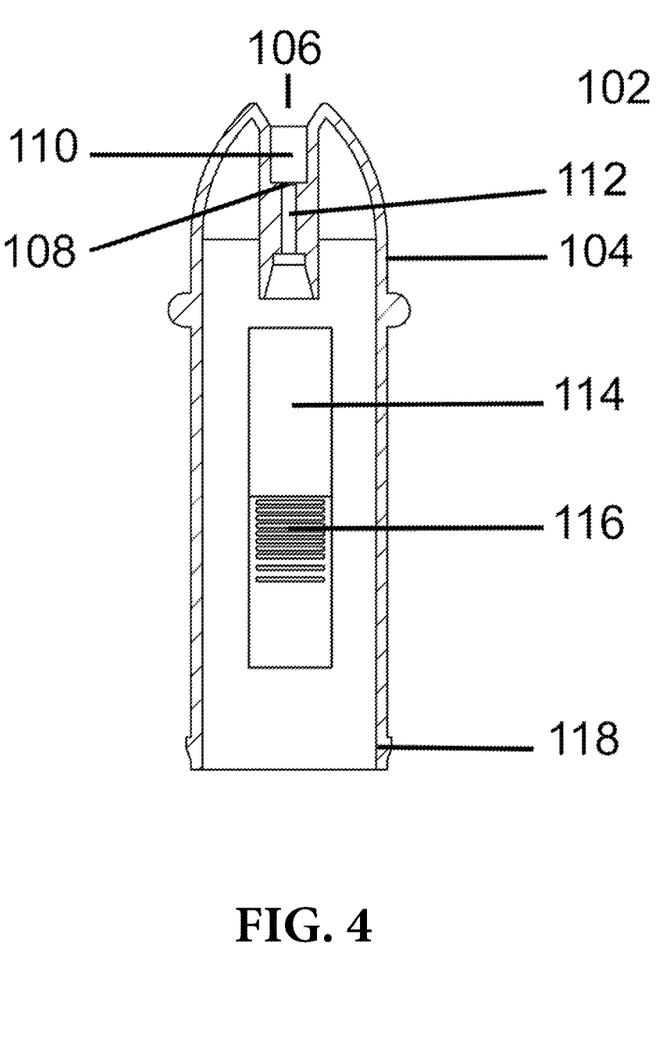
FIG. 4 is a cross-sectional view of the actuator.

FIG. 4 is a cross-sectional view of actuator 102, with actuator receptacle locking clip 118 once snapped into receptacle canister security ridges 152 of receptacle housing 144 (not shown in FIG. 4) creates a one-piece aerosol pressurized inhaler delivery device 100. Actuator 102 is designed to release a known amount of liquid propellant 164 and micellized liquid nicotine formula 166 (not shown) through metered valve 128 (not shown) positioned on actuator valve sleeve 112. Once actuator discharge finger slide control 114 having grip ridges 116, is depressed downward, liquid propellant 164 and micellized liquid nicotine formula 166 (not shown) pass through actuator discharge nozzle 108, actuator discharge channel 110, and uniformly recessed actuator discharge area 106 allowing liquid propellant 168 and micellized liquid nicotine formula 166 (not shown) to be expelled as a fine nano mist spray with particle size of approximately 5 μm to 8 μm (microns) inhaled from actuator mouthpiece 104.

Figure 5:
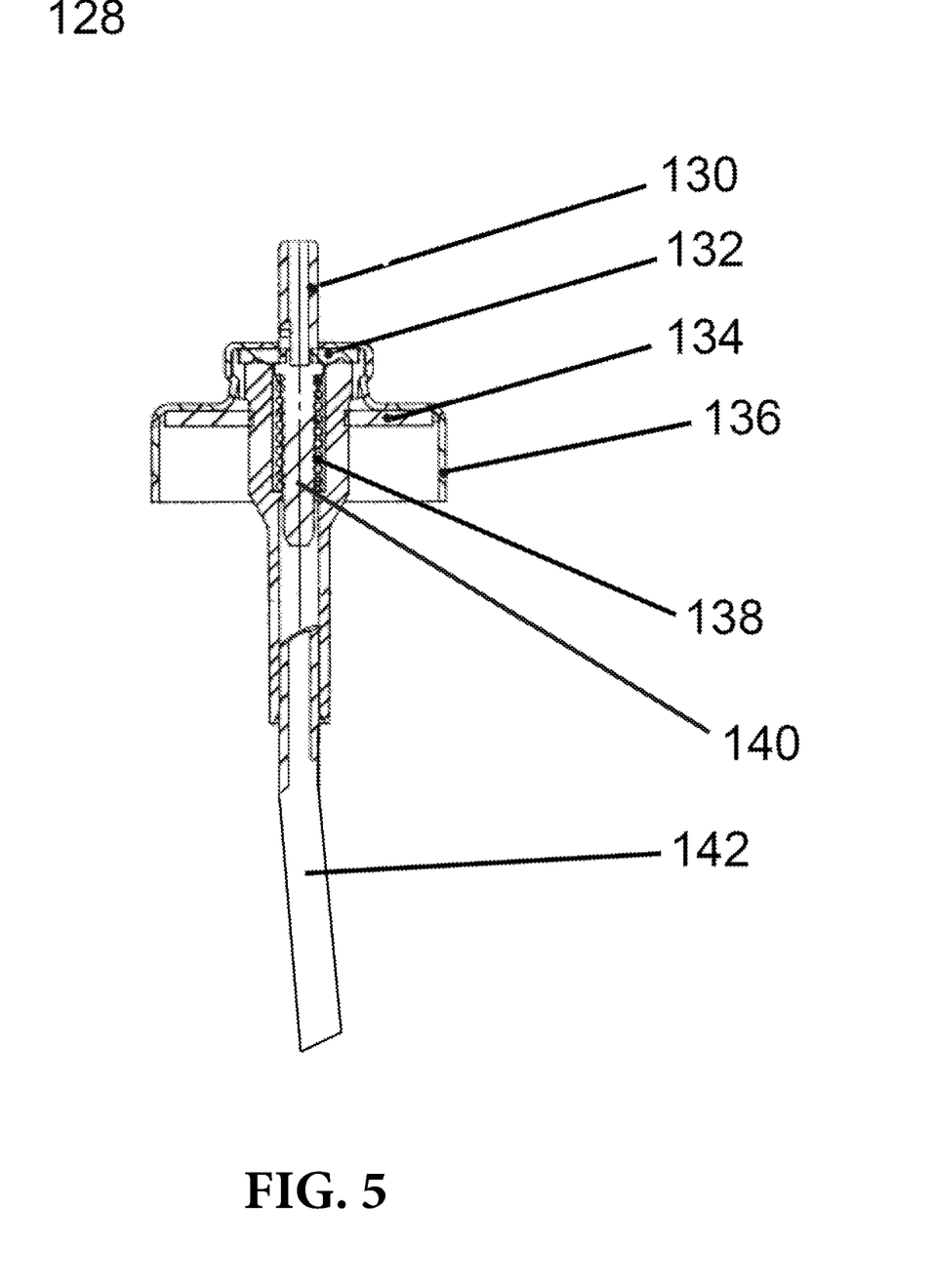
FIG. 5 is a cross-sectional view of the metered valve.

FIG. 5 is a cross-sectional view of metered valve 128 to be crimped onto aluminum canister 156 (not shown) via metered valve mounting cup 136. Once liquid propellant 164 (not shown) is introduced into aluminum canister 156 (not shown) pressure is created and micellized liquid nicotine formula 166 and liquid propellant 164 (not shown) is expelled through metered valve metering chamber 140 drawn up from metered valve dip tube 142. Once actuator discharge finger slide control 114 (not shown) is depressed metered valve stem 130 is pushed downward past metered valve internal gasket 132 and metered valve external gasket 134 overcoming resistance from metered valve spring 138 allowing micellized liquid nicotine formula 166 and liquid propellant 164 (not shown) to be expelled through actuator 102 (not shown).

Figure 6:
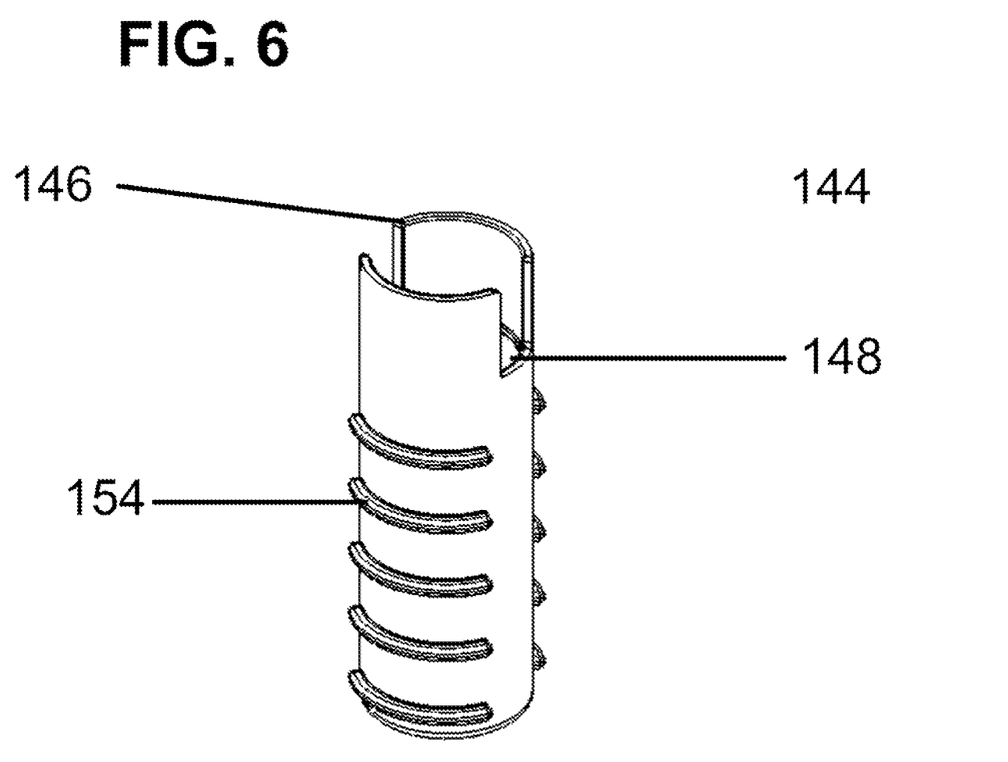
FIGS. 6-7 provide various isometric views of the receptacle housing.
Figure 7:
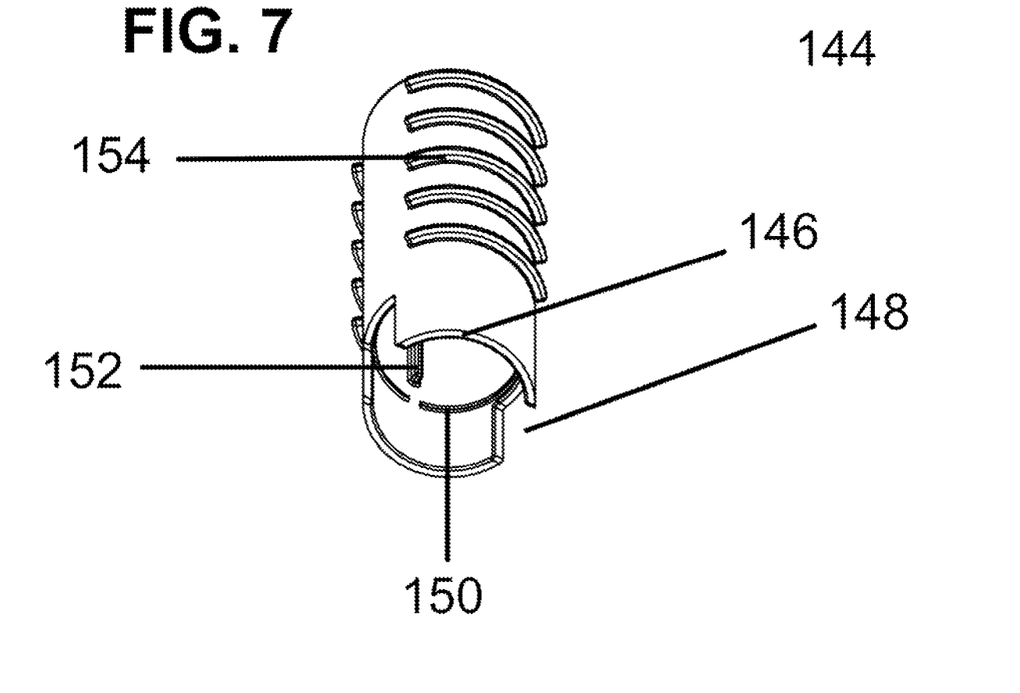

FIGS. 6-7 is an isometric side and vertical view of receptacle housing 144 showing receptacle actuator locking edge 150 once pushed together with actuator receptacle locking clip 118 (not shown) creates a one-piece aerosol pressurized inhaler delivery device 100 (not shown). Receptacle housing actuator rim 146 fits outside and firmly against actuator 100 (not shown), allowing three receptacle canister security ridges 152 to hold aluminum canister 156 (not shown) securely inside receptacle housing 144. Receptacle housing finger slide control channels 148 allow depression of actuator discharge finger slide control 114 (not shown) and or actuator discharge finger slide control child proof safety guard 120 (not shown) to be inserted into receptacle housing finger slide control channels 148 creating a child proof safety inhalation pressurized delivery device. Receptacle housing 144 can be held securely by grasping receptacle cylindrical grips 154.

Figures 8, 9:
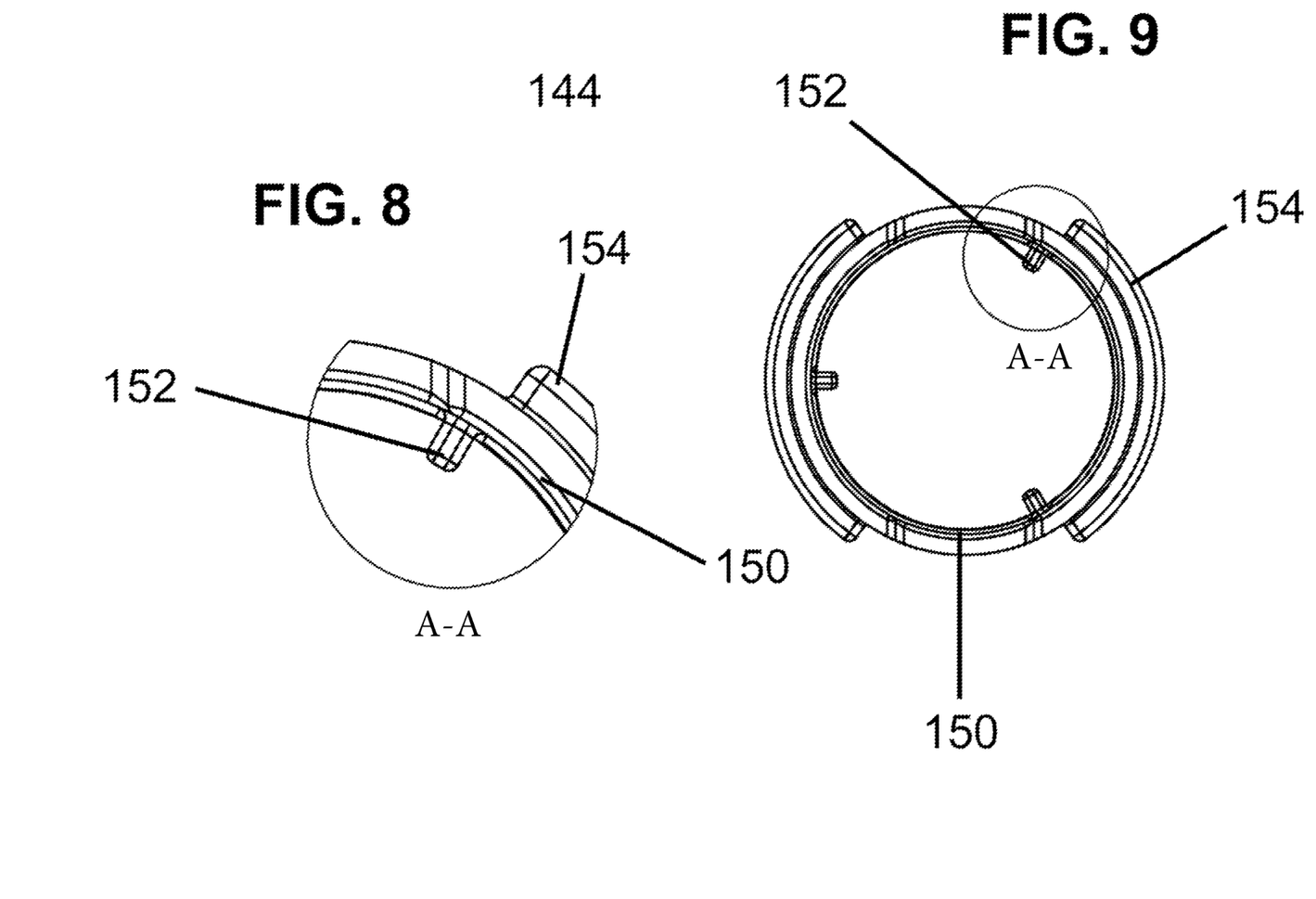
FIG. 8 is a top view of the receptacle housing.
FIG. 9 is an enlarged view of the receptacle housing.

FIGS. 8-9 is a top view of receptacle housing 144, showing receptacle cylinder grips 154, receptacle actuator locking edge 150 and enlarged view of receptacle canister security ridges 152. Aluminum canister 156 (not shown) pushed into receptacle housing 144 is secured with pressure created between sides of aluminum canister 156 (not shown) and receptacle canister security ridges 152. Actuator 102 (not shown) is locked into receptacle housing 144 when pushed downward engaging actuator receptacle locking clip 118 (not shown) with receptacle actuator locking edge 150.

Figure 10:
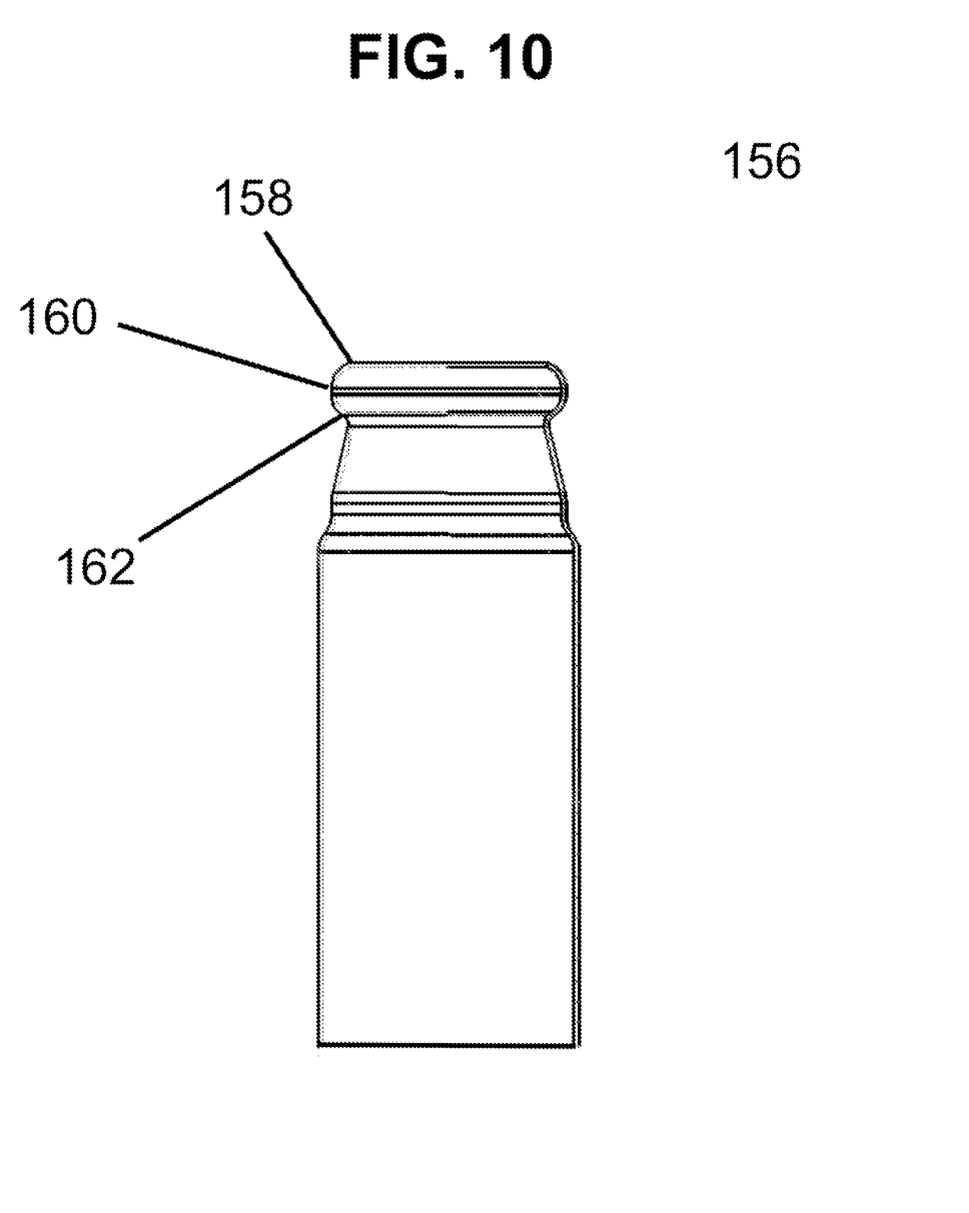
FIG. 10 is a side view of the aluminum canister.

FIG. 10 shows a side view of aluminum canister 156 where metered valve 128 (not shown) resides over aluminum canister lip 158 and aluminum canister throat 160 and under aluminum canister rim 162. When metered valve 128 (not shown) is crimped to aluminum canister 156, metered valve mounting cup 136 (not shown) is held firmly against aluminum canister rim 162.

Figure 11:
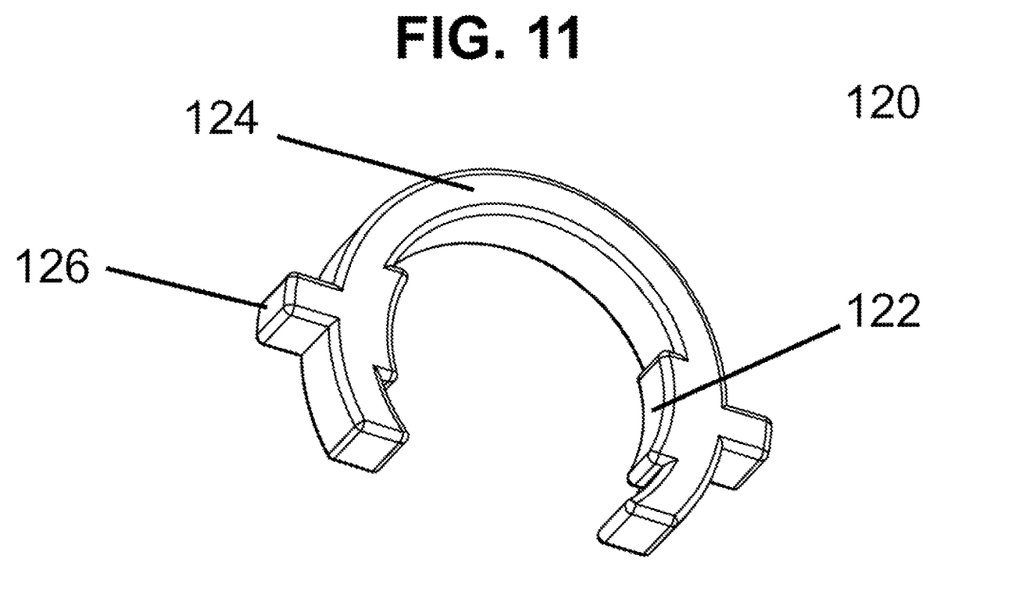
FIGS. 11-12 are isometric view of the actuator discharge finger slide control child proof safety guard.
Figure 12:
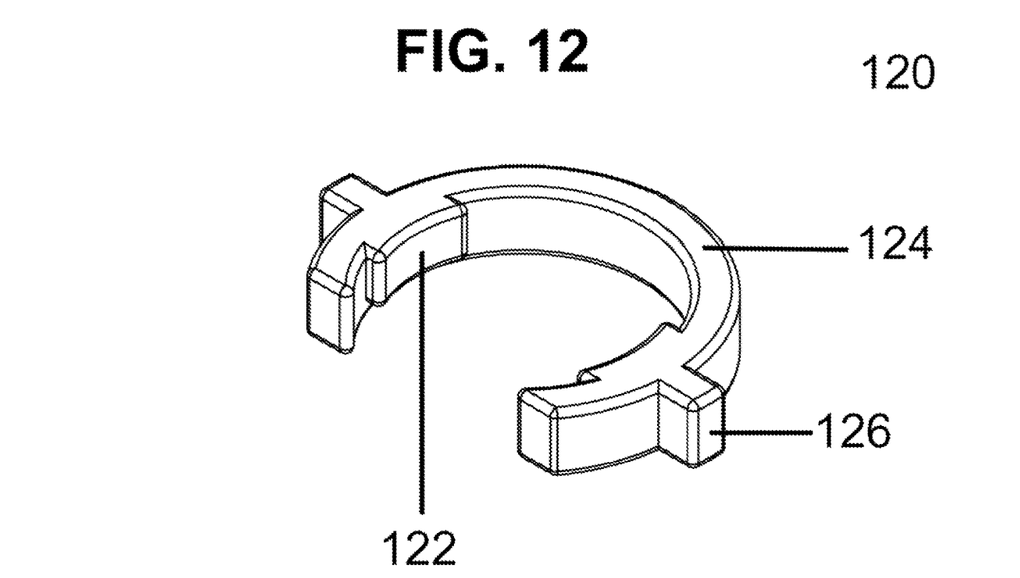

FIGS. 11-12 include isometric views of actuator discharge finger slide control child proof safety guard 120 comprising child proof safety guard locks 122, child proof safety guard plastic compression clip 124 and child proof safety guard grips 126.

Figure 13:
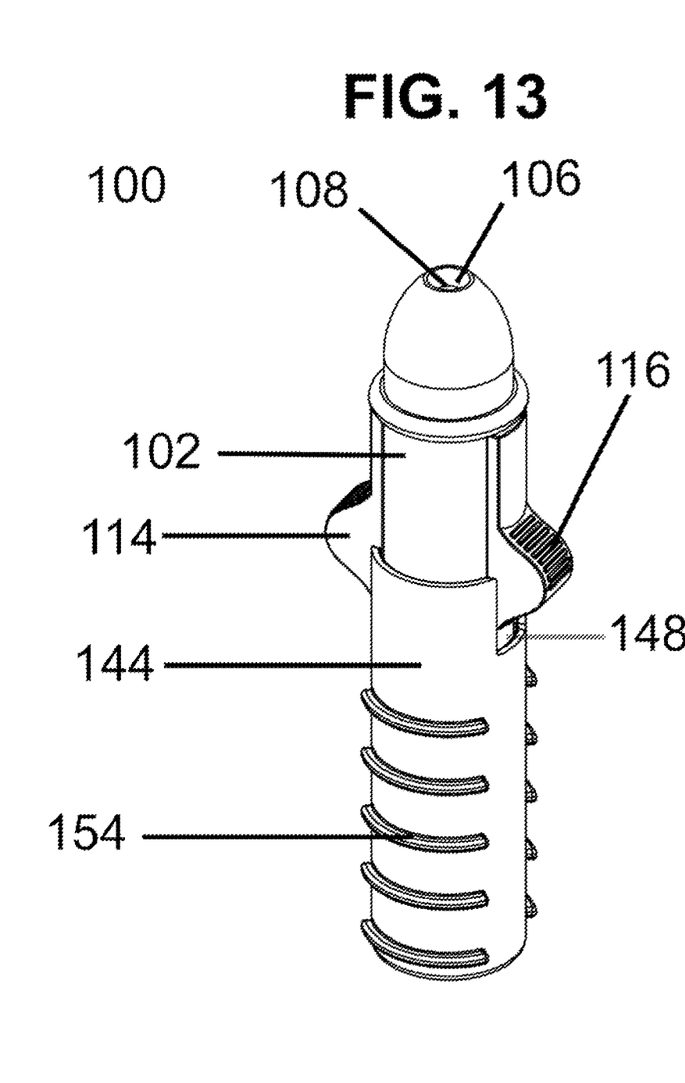
FIGS. 13-14 are isometric views of an assembled delivery device with and without a discharge control/safety guard attached.

FIG. 13 is an isometric view of aerosol pressurized inhaler delivery device 100 showing actuator 102 locked into receptacle housing 144. Actuator discharge finger slide control 114, having grip ridges 116, when pushed downward into receptacle housing finger slide control channels 148 discharges micellized liquid nicotine formula 166 and liquid propellant 164 (not shown) through actuator discharge nozzle 108 and actuator discharge area 106 of actuator 102. Receptacle housing 144 has ergonomic designed receptacle cylinder grips 154 providing comfortable grip to receptacle housing 144.

Figure 14:
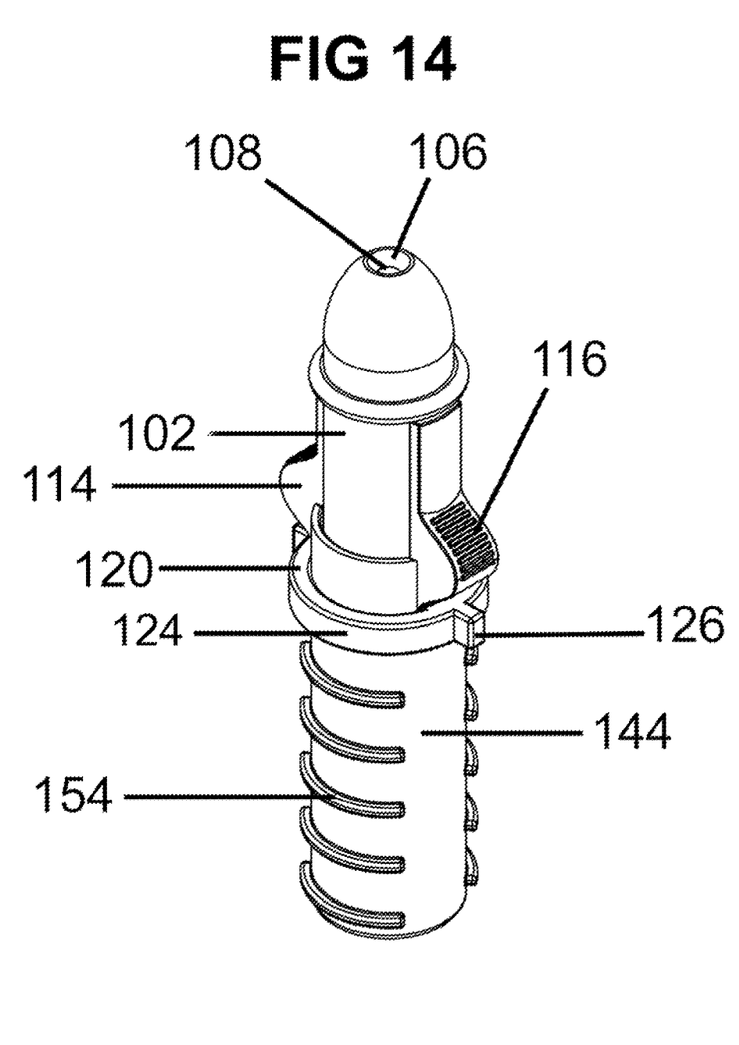

FIG. 14 is an isometric view of assembled child proof aerosol pressurized inhaler delivery device 100, comprising actuator 102, receptacle housing 144, actuator discharge finger slide control 114 having grip ridges 116, and discharge finger slide control child proof safety guard 120 held into place by child proof safety guard locks 122 (not visible) positioned over receptacle housing finger slide control channels 148 (not visible) once child proof guard plastic compression clip 124 is opened by depressing child proof safety guard grips 126.

Figure 15:
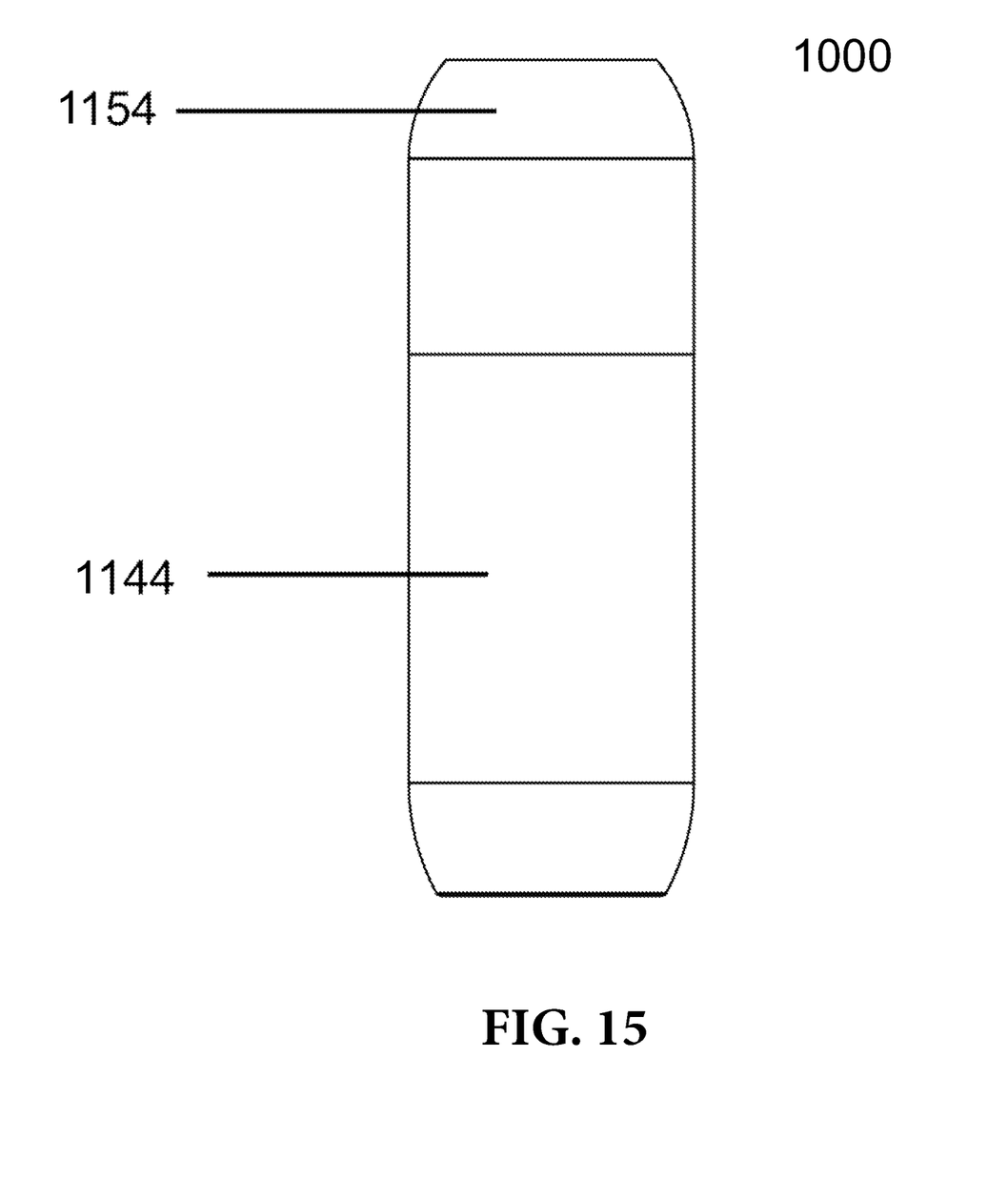
FIG. 15 is a side elevation view of a delivery device according to another embodiment of the present disclosure.

FIG. 15 is a side view of an aerosol nano mist vapor delivery device 1000 according to yet another embodiment. The delivery device according to this embodiment may comprise a resistant cap 1154 attached to protective plastic canister receptacle housing 1144. As with the previous embodiment, the delivery device assembly may comprise an aluminum canister, preferably containing micellized liquid nicotine formula, and at least one (preferably liquid) propellant with a metered valve crimped onto aluminum canister. The assembly may also comprise an actuator positioned on metered valve, despite not being physically shown in FIG. 15.

Figure 16:
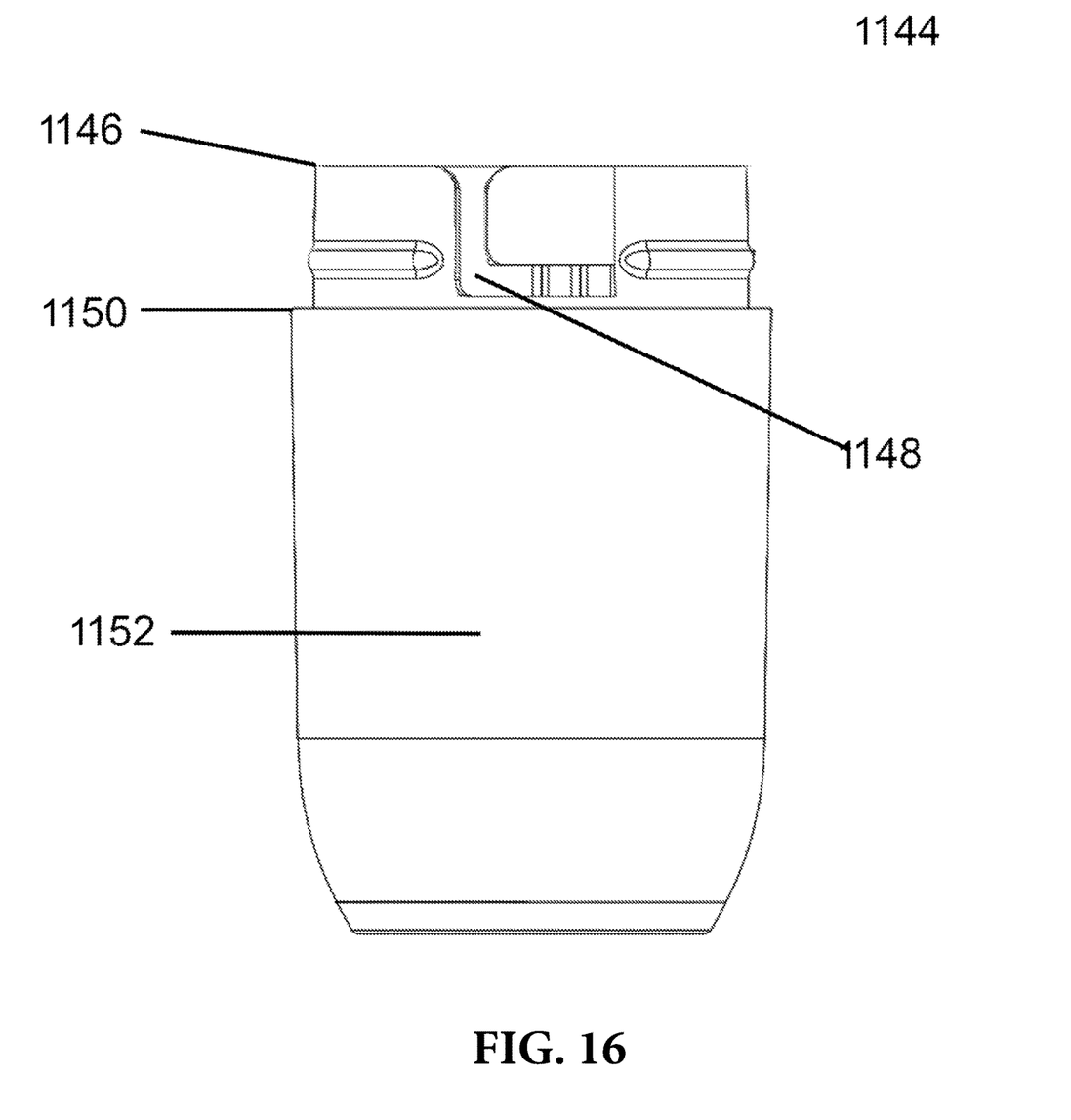
FIG. 16 is a side elevation view of a first portion of the delivery device shown in FIG. 15.
Figure 17:
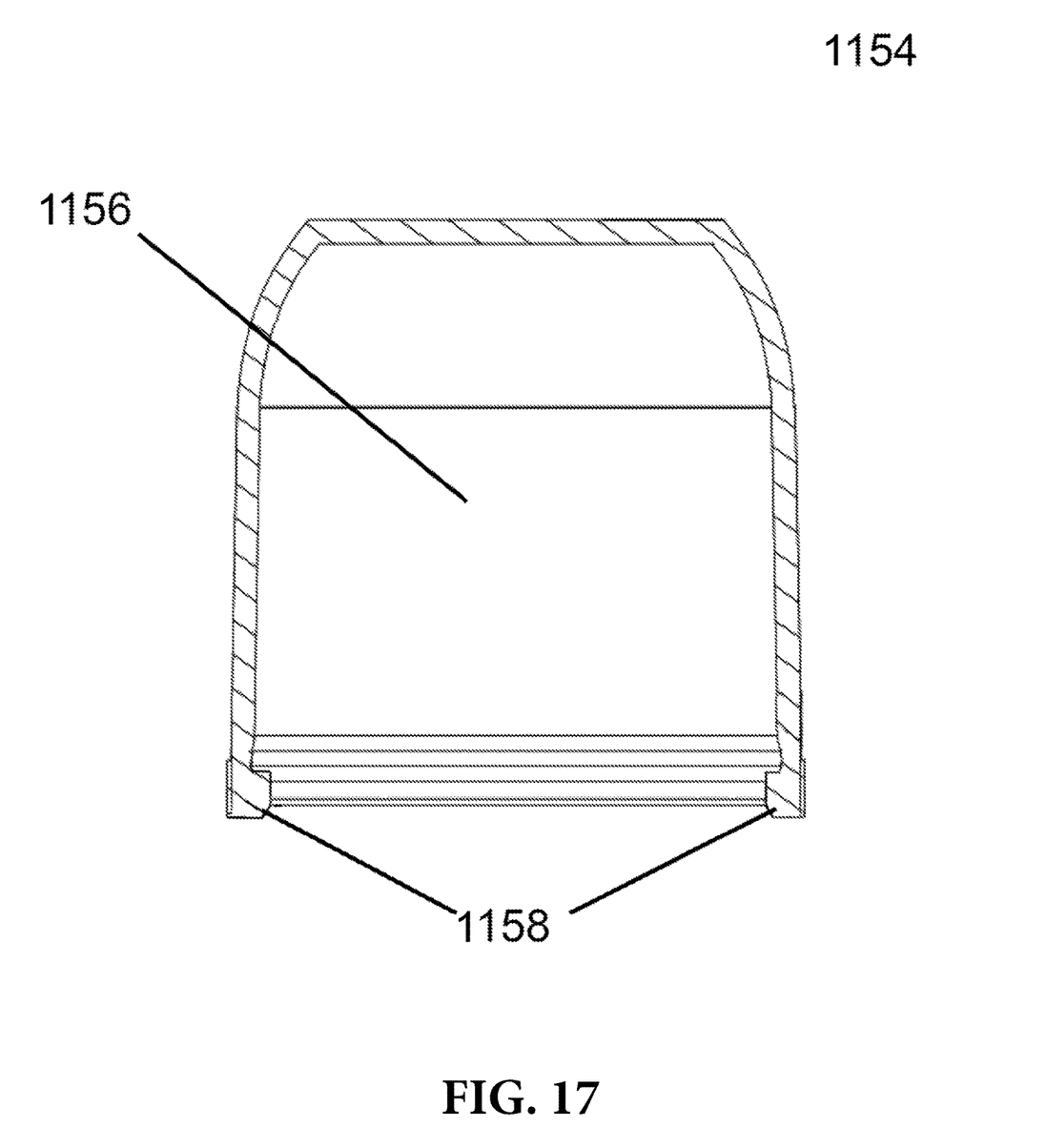
FIG. 17 is a cross-sectional view of a second portion of the delivery device shown in FIG. 15.

FIG. 16 is a side elevation view of a first portion of the delivery device 1000 shown in FIG. 15. As mentioned, the delivery device assembly may comprise a protective housing 1144 for housing the canister and other components, and may further comprise a protective canister base 1152, plastic base receptacle recessed lip 1150, plastic base receptacle child resistant cap channels 1148 and plastic base receptacle rim 1146. FIG. 17 is a cross-sectional view, this time depicting a second portion of the delivery device 1000 shown in FIG. 15. The delivery device 1000 may comprise a protective child resistant cap 1154 that mates with the protective canister base 1152 and forms a secure closure about plastic base receptacle rim 1146. The child resistant cap 1154 may be comprised of a cap base 1156 and may further comprise one or more resistant (i.e., interference fit) ribs 1158.

FIGS. 1-17 may depict more than all of the components required to operate the device. It is also understood that the device design may comprise additional surface features in certain embodiments than those shown in FIGS. 1-17, including surface texturing, coloring, packaging, ergonomic shape, contouring, sheathing, etc. Thus, the design of FIGS. 15-17 is exemplary and non-limiting as to the scope of the present disclosure.

With respect to the embodiments described above, it is expressly understood that such embodiments may be incorporated for use in practicing the novel methods described herein. In certain embodiments, those methods may comprise greater or fewer steps than as described above. By way of example, but not limitation, one step for use with the various embodiments described above may comprise the step of removing and replacing the canister or securing a safety guard, with different steps included in the method of operation provided accordingly. Thus, variations on this and other steps, and the inclusion or exclusion of additional steps described herein, are expressly contemplated by the present disclosure.

It is expressly understood that where the term "consumer" has been used to describe the various embodiments of the disclosure, the term should not be construed as limiting in any way. For instance, a consumer could be a human user or, in a veterinary application, an animal. Therefore, it is intended that the device and methods described herein apply equally to veterinary science as they would if practiced on a human being. The apparatus and methods described herein therefore have application beyond controlled dosage of nicotine, by way of example.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. For further illustration, the information and materials supplied with the provisional application from which this application claims priority is expressly made a part of this disclosure and incorporated by reference herein in their entirety. This form of disclosure, therefore, is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An encapsulated pressurized inhalation delivery device comprising:
   protective housing, comprising:
     a base portion comprising a recessed lip;
     a cap portion dimensioned to receive the recessed lip of the base portion such that the base portion and cap portion are connected and aligned along a common axis; and
     the base portion and cap portion both comprise an internal void; and
   a pressurized inhalation device comprising:
     a mouthpiece integral with an actuator;
     a metered valve;
     a metal canister; and
     a cylindrical receptacle housing:
   wherein the metal canister contains a micellized liquid formula and a propellant:
   wherein the metered valve is crimped to the metal canister;
   wherein the actuator is generally cylindrical and has an actuator discharge nozzle;
   wherein the actuator is in contact with and supported by a surface of the metered valve, and is movably coupled to the cylindrical receptacle housing;
   wherein the metal canister is positioned within the cylindrical receptacle housing;
   wherein the mouthpiece, metal canister, metered valve actuator and receptacle housing are all in alignment about the common axis;
   wherein the pressurized inhalation device is positioned within the internal void; and
   wherein the actuator and the metered valve are configured such that, upon axial movement of the actuator with respect to the metered valve, in the direction of the cylindrical receptacle housing, a predetermined dosage of micellized liquid formula is supplied from the metal canister.

2. The encapsulated pressurized inhalation delivery device of claim 1 further comprising one or more finger slide controls for movement of the actuator.

3. The encapsulated pressurized inhalation delivery device of claim 1, wherein the micellized liquid formula comprises at least a micellized liquid nicotine formula.

4. The encapsulated pressurized inhalation delivery device of claim 1, wherein the predetermined dosage of micellized liquid formula is delivered through the actuator discharge nozzle.

5. The encapsulated pressurized inhalation delivery device of claim 4, wherein the predetermined dosage of micellized liquid formula is in the range of 50 to 100 microliters.

6. The encapsulated pressurized inhalation delivery device of claim 4, wherein the predetermined dosage of micellized liquid formula is 100 microliters.

7. The encapsulated pressurized inhalation delivery device of claim 4, wherein the predetermined dosage of micellized liquid formula is 65 microliters.

8. The encapsulated pressurized inhalation delivery device of claim 4, wherein the micellized liquid formula comprises at least a nicotine salt.

\* \* \* \* \*